United States Patent
McLeod et al.

(10) Patent No.: US 12,343,095 B2
(45) Date of Patent: Jul. 1, 2025

(54) SYSTEMS AND METHODS FOR PROVIDING SURGICAL ASSISTANCE BASED ON OPERATIONAL CONTEXT

(71) Applicant: Intuitive Surgical Operations, Inc., Sunnyvale, CA (US)

(72) Inventors: A. Jonathan McLeod, Sunnyvale, CA (US); Maximilian H. Allan, San Francisco, CA (US); Mahdi Azizian, San Jose, CA (US); Daniel Proksch, San Jose, CA (US); Pourya Shirazian, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 475 days.

(21) Appl. No.: 17/781,251

(22) PCT Filed: Jan. 13, 2021

(86) PCT No.: PCT/US2021/013277
§ 371 (c)(1),
(2) Date: May 31, 2022

(87) PCT Pub. No.: WO2021/146313
PCT Pub. Date: Jul. 22, 2021

(65) Prior Publication Data
US 2022/0409300 A1 Dec. 29, 2022

Related U.S. Application Data

(60) Provisional application No. 62/961,542, filed on Jan. 15, 2020.

(51) Int. Cl.
*A61B 34/00* (2016.01)
*A61B 34/20* (2016.01)
(Continued)

(52) U.S. Cl.
CPC .............. *A61B 34/25* (2016.02); *A61B 34/37* (2016.02); *G06T 7/0012* (2013.01); *G06V 20/50* (2022.01);
(Continued)

(58) Field of Classification Search
CPC . A61B 34/25; A61B 34/37; A61B 2034/2059; A61B 2034/2065;
(Continued)

(56) References Cited

U.S. PATENT DOCUMENTS

| | | | |
|---|---|---|---|
| 9,646,423 B1 | 5/2017 | Sun et al. | |
| 2009/0036902 A1* | 2/2009 | DiMaio | A61B 8/12 606/130 |

(Continued)

FOREIGN PATENT DOCUMENTS

EP    3242590 A1    11/2017

OTHER PUBLICATIONS

International Search Report and Written Opinion for Application No. PCT/US2021/013277, mailed May 3, 2021, 11 pages.
(Continued)

*Primary Examiner* — Brian T Gedeon

(57) ABSTRACT

An exemplary contextual assistance system identifies, during a surgical procedure, an operational context of the surgical procedure while a particular object is present at a surgical site depicted by a first version of an image. Based on the identified operational context, the contextual assistance system augments a depiction of the particular object within a second version of the image that is presented to a user associated with the surgical procedure. Corresponding systems and methods are also disclosed.

20 Claims, 10 Drawing Sheets

(51) Int. Cl.
  *A61B 34/37* (2016.01)
  *G06T 7/00* (2017.01)
  *G06V 20/50* (2022.01)
  *G16H 20/40* (2018.01)

(52) U.S. Cl.
  CPC ............ *A61B 2034/2059* (2016.02); *A61B 2034/2065* (2016.02); *G06T 2207/30004* (2013.01); *G06V 2201/03* (2022.01)

(58) Field of Classification Search
  CPC ........ G06T 7/0012; G06T 2207/30004; G06V 20/50; G06V 2201/03; G16H 20/40
  See application file for complete search history.

(56) References Cited

U.S. PATENT DOCUMENTS

| | | | |
|---|---|---|---|
| 2009/0088634 A1* | 4/2009 | Zhao | A61B 1/00193 600/425 |
| 2015/0366628 A1* | 12/2015 | Ingmanson | A61B 5/015 600/424 |
| 2016/0287337 A1 | 10/2016 | Aram et al. | |
| 2017/0071681 A1* | 3/2017 | Peine | A61B 34/74 |
| 2018/0082480 A1 | 3/2018 | White et al. | |
| 2018/0200004 A1* | 7/2018 | Carnes | A61B 90/37 |
| 2019/0114768 A1 | 4/2019 | Carnes et al. | |
| 2019/0231432 A1* | 8/2019 | Amanatullah | A61B 90/361 |
| 2021/0228276 A1* | 7/2021 | Giraldez | G09B 1/00 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2021/013277, mailed on Jul. 28, 2022, 08 pages.

\* cited by examiner

SYSTEMS AND METHODS FOR PROVIDING SURGICAL ASSISTANCE BASED ON OPERATIONAL CONTEXT

RELATED APPLICATIONS

The present application is a U.S. National Stage Application under 35 U.S.C. § 371 of International Application No. PCT/US2021/013277, filed on Jan. 13, 2021, which claims priority to U.S. Provisional Patent Application No. 62/961,542, filed Jan. 15, 2020, the contents of which are hereby incorporated by reference in their entirety.

BACKGROUND INFORMATION

An imaging device such as an endoscope may be used to capture imagery viewable at a surgical site (e.g., a surgical space within a body of a patient) during a surgical procedure. Data representative of such imagery may be presented to a surgeon and/or others on a surgical team performing the surgical procedure to thereby provide visibility of the surgical site to the surgeon and team members as they perform the surgical procedure. As the surgical procedure proceeds from one phase to another, various different things may come into and go out of view in an image feed captured by the imaging device. Some of these things visible at the surgical site may be helpful and important for the team members to see clearly, while other things may be unimportant or even distracting or otherwise undesirable for the team members to see. Moreover, the imagery that is important and unimportant or distracting may dynamically change based on the operational context of the surgical procedure from phase to phase and from moment to moment during the procedure.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions and a processor communicatively coupled to the memory and configured to execute the instructions. For example, during a surgical procedure, the processor may identify an operational context of the surgical procedure while a particular object is present at a surgical site depicted by a first version of an image. Based on the identified operational context, the processor may augment a depiction of the particular object within a second version of the image that is presented to a user associated with the surgical procedure.

An exemplary method is performed by a contextual assistance system during a surgical procedure. The method includes identifying an operational context of the surgical procedure while a particular object is present at a surgical site depicted by a first version of an image. The method further includes augmenting, based on the identified operational context, a depiction of the particular object within a second version of the image that is presented to a user associated with the surgical procedure.

An exemplary non-transitory computer-readable medium stores instructions that, when executed, direct a processor of a computing device to perform various operations during a surgical procedure. For example, the instructions may direct the processor to identify an operational context of the surgical procedure while a particular object is present at a surgical site depicted by a first version of an image. The instructions may further direct the processor to augment, based on the identified operational context, a depiction of the particular object within a second version of the image that is presented to a user associated with the surgical procedure.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
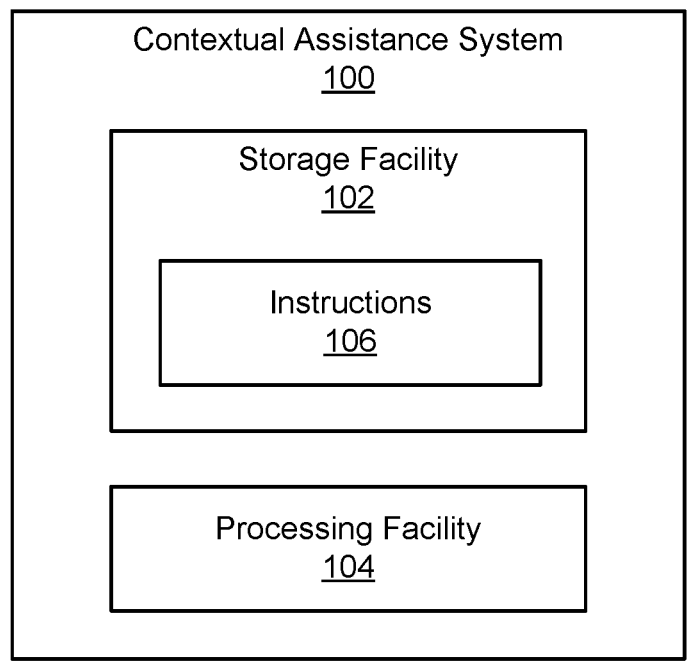
FIG. 1 illustrates an exemplary contextual assistance system for providing surgical assistance based on operational context of a surgical procedure according to principles described herein.

Systems and methods for providing surgical assistance based on operational context of a surgical procedure are described herein. In many cases, surgical procedures are planned ahead of time to be performed in different procedural phases that each are associated with different tasks, objectives, challenges, and so forth. As mentioned above, it may be helpful for certain elements (e.g., certain tissues or other anatomical structures, certain instruments or other objects at the surgical site, certain virtual models or other augmentations, etc.) to be viewed under particular sets of circumstances (e.g., during certain procedural phases of the surgical procedure) while other elements may be more helpful to be viewed under other circumstances.

To this end, contextual assistance systems and methods described herein may employ any suitable type of extended reality technology (e.g., an augmented reality technology, a virtual reality technology, a mixed reality technology, etc.) to maximize visibility and facilitate operational effectiveness of a surgical procedure in a manner that is context-specific to the surgical procedure. For example, various contextual aspects of the surgical procedure (e.g., what objects are present at a surgical site, what procedural phase of the surgical procedure is currently being undertaken, etc.) may be detected. Then, based on this context, augmentations presented by the extended reality technology can be used to highlight or emphasize objects presented to the surgical team in ways that facilitate the surgical procedure.

As one example, an exemplary contextual assistance system may be configured to identify, during a surgical procedure, an operational context of the surgical procedure. For example, the operational context may relate to the current procedural phase of the surgery, various objects (e.g., instruments, obscurants, specific tissues, etc.) that are present at a surgical site, and/or any other contextual aspects that may be in play during the surgical procedure. The identification of the operational context may be performed while the particular object is present at a surgical site depicted by a first version of an image. As such, based on the identified operational context, the contextual assistance system may augment a depiction of the particular object within a second version of the image that is presented to a user associated with the surgical procedure. For example, an augmented image that helpfully emphasizes, highlights, adds to, simplifies, or otherwise augments the original image may be generated and provided for viewing by surgical team members to facilitate the surgical operation they are performing.

By way of illustration, a surgical procedure known as a partial nephrectomy will be considered, although it will be understood that the principles described may apply to a wide array of different surgical procedures other than partial nephrectomies.

The ultimate objective of a partial nephrectomy is to remove a portion of a kidney from a patient (e.g., to excise a tumor growing on the kidney or the like) without removing the entire kidney. To this end, this surgical procedure may include a first exemplary procedural phase in which the surgical team does not yet have a view of the kidney, a second exemplary procedural phase in which the team has exposed the kidney and is beginning to manipulate the tissue of the kidney, a third exemplary procedural phase during which dissection of the hilum is performed, and various other exemplary procedural phases that may come before, after, or between these exemplary procedural phases.

During the first exemplary procedural phase in which the surgical team does not have access to the kidney, it may be distracting or otherwise undesirable to present three-dimensional ("3D") models of the kidney to the surgeon or other surgical team members, or to prompt these users to interact with such models. Accordingly, the contextual assistance system may abstain from presenting any such models under these circumstances during this procedural phase.

Once the kidney has been exposed in the second exemplary procedural phase, however, it may be effective and helpful for the surgical team to begin viewing a predefined 3D model of the kidney (e.g., a model generated based on preoperative imaging, etc.), possibly with added emphasis on relevant parts of the model (e.g., edges of the paranchyma or other anatomical structures useful in getting a good alignment). A presentation of the 3D model of the kidney, together with prompts for user interaction to properly register the model to the kidney in the image feed, may hence be appropriate and desirable at this stage, and the contextual assistance system may alter the image feed provided to the surgical team to include such augmentations.

During the third exemplary procedural phase when the surgeon begins dissecting the hilum, it may be helpful for emphasis of the model to now be on renal vasculature or other components relevant to this specific procedural phase. Likewise, it may be desirable at this stage to hide elements that are not useful or that would be distracting to the task at hand. Accordingly, the contextual assistance system may now alter the images being provided for viewing by the surgical team to show and/or highlight certain elements while hiding and/or removing emphasis from other elements as may be most useful to the surgical team in the current context and circumstances.

By customizing the augmentations provided to the user based on the operational context of the surgical procedure in this way, contextual assistance systems and methods described herein may provide significant surgical assistance to the surgical team, along with various other advantages and benefits. Specifically, for example, systems and methods described herein for providing surgical assistance based on operational context may facilitate surgical teams in performing tasks efficiently and effectively by increasing the visibility of the most relevant imagery and/or decreasing the visibility of less relevant imagery. This may be particularly helpful in situations in which various obscurants present at the surgical site (e.g., smoke, blood, fat, etc.) may otherwise limit the surgeon's visibility. Moreover, by augmenting the view of the surgical site that is presented to different users in ways that are customized to those users specifically and to the operational context of the procedure, the users may be less distracted and may more easily focus on the most important aspects needed to perform specific tasks effectively, efficiently, and conveniently.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary contextual assistance system 100 ("system 100") for providing surgical assistance based on operational context of a surgical procedure according to principles described herein. In certain examples, system 100 may be included in, implemented by, or connected to one or more components of a computer-assisted surgical system such as an exemplary computer-assisted surgical system that will be described below in relation to FIG. 2. For instance, in such examples, system 100 may be implemented by one or more components of a computer-assisted surgical system such as a manipulating system, a user control system, or an auxiliary system. In other examples, system 100 may be implemented by a stand-alone computing system (e.g., a stand-alone computing system communicatively coupled to a computer-assisted surgical system or implementing another non-surgical application or use case).

As shown in FIG. 1, system 100 may include, without limitation, a storage facility 102 and a processing facility 104 selectively and communicatively coupled to one another. Facilities 102 and 104 may each include or be implemented by one or more physical computing devices including hardware and/or software components such as processors, memories, storage drives, communication interfaces, instructions stored in memory for execution by the processors, and so forth. Although facilities 102 and 104 are shown to be separate facilities in FIG. 1, facilities 102 and 104 may be combined into fewer facilities, such as into a single facility, or divided into more facilities as may serve a particular implementation. In some examples, each of facilities 102 and 104 may be distributed between multiple devices and/or multiple locations as may serve a particular implementation.

Storage facility 102 may maintain (e.g., store) executable data used by processing facility 104 to perform any of the functionality described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with providing surgical assistance based on operational context of a surgical procedure. For example, processing facility 104 may be configured to detect, during a surgical procedure, that a particular object is present at a surgical site depicted by a first version of an image. For example, the particular object may be an anatomical structure (e.g., a portion of tissue, etc.), a mechanical object (e.g., a surgical instrument or other tool used to perform the surgical procedure, etc.), or another type of visible object present at the surgical site. The first version of the image may be captured by an imaging device present at the surgical site (e.g., an endoscopic imaging device or other suitable imaging device) and may depict a view of the surgical site (including a depiction of the particular object) from a vantage point of the imaging device. While various examples of how the particular object may be explicitly detected by the system are described herein, it will be understood that, in certain examples, processing facility 104 may not actively perform any function or operation to explicitly detect the presence of the particular object, particularly if the object is one that may be assumed to be present at the surgical site without being actively detected (e.g., vasculature of the patient, etc.). In such cases, processing facility 104 may forego an active operation for detecting the presence of the object in favor of proceeding with an implicit assumption that the object is known to be present at the surgical site.

Also during the surgical procedure, processing facility 104 may identify an operational context of the surgical procedure. As used herein, the "operational context" of a particular surgical procedure may refer to any circumstance, event, or condition associated with the surgical procedure, or other any other such aspect of the surgical procedure. In some examples, the operational context may correspond to a particular moment in time, such as a moment in time when the operational context is identified. In various examples, the operational context of a surgical procedure may relate to a procedural phase of the surgical procedure (e.g., selected from a plurality of predefined procedural phases set forth when the surgical procedure is planned, identified dynamically and less formally during the surgical procedure, etc.), to one or more tasks being performed as part of the surgical procedure, to physical objects (e.g., mechanical objects such as instruments or tools, anatomical structures, obscurants, etc.) that are detected to be present at the surgical site, to virtual objects (e.g., augmentations, etc.) that are displayed to the user to appear to be present at the surgical site, and/or to any other contextual aspects, conditions, events, or circumstances as may be associated with the surgical procedure at a particular point in time.

In certain examples, processing facility 104 may identify the operational context while the particular object is present at the part of the surgical site depicted by the first version of the image, such that the particular object is depicted within the image. As described above, the operational context of the surgical procedure at a particular time may relate to any of various aspects of the surgical procedure including an ongoing procedural phase of the surgical procedure at the particular time, a task being performed at the surgical site at the particular time, which objects (e.g., instruments, tools, etc.) are present at the surgical site at the particular time, whether obscurants (e.g., smoke, blood, fat, instruments, tissue, etc.) are obscuring the view of a significant element at the surgical site at the particular time, or any other suitable contextual circumstance of the surgical site at the particular time.

Based on the identified operational context, processing facility 104 may augment a depiction of the particular object within a second version of the image. In some examples, this augmentation may be performed while the surgical procedure is still ongoing so as to allow a user associated with the surgical procedure (e.g., a surgeon or other surgical team member helping to perform the surgical procedure) to be presented with the second, augmented version of the image in real time. In this way, as the user performs or otherwise facilitates the surgical procedure, he or she may view the second version of the image and be able to more clearly see the particular object than he or she would be able to if not for the augmentation performed by system 100. Accordingly, the user may be assisted in performing his or her job at an optimum level based on the augmented image provided by system 100.

As has been described, system 100 may be configured to provide surgical assistance based on operational context during a surgical procedure. As used herein, an operation will be understood to be performed during a surgical procedure if the operation is performed while the surgical procedure is ongoing, such as before imaging equipment and/or surgical instruments are withdrawn from the body, before the body is stitched up and/or brought out of anesthesia (if applicable to the surgical procedure), and so forth. To this end, operations described herein may be performed in real time (i.e., performed immediately and without undue delay, such as by processing dynamic and time-sensitive data including captured depth data while the data remains relevant and up-to-date).

The operations described above, as well as other operations that may be performed by processing facility 104, are described in more detail herein. In the description that follows, any references to functions performed by system 100 may be understood to be performed by processing facility 104 based on instructions 106 stored in storage facility 102.

Figure 2:
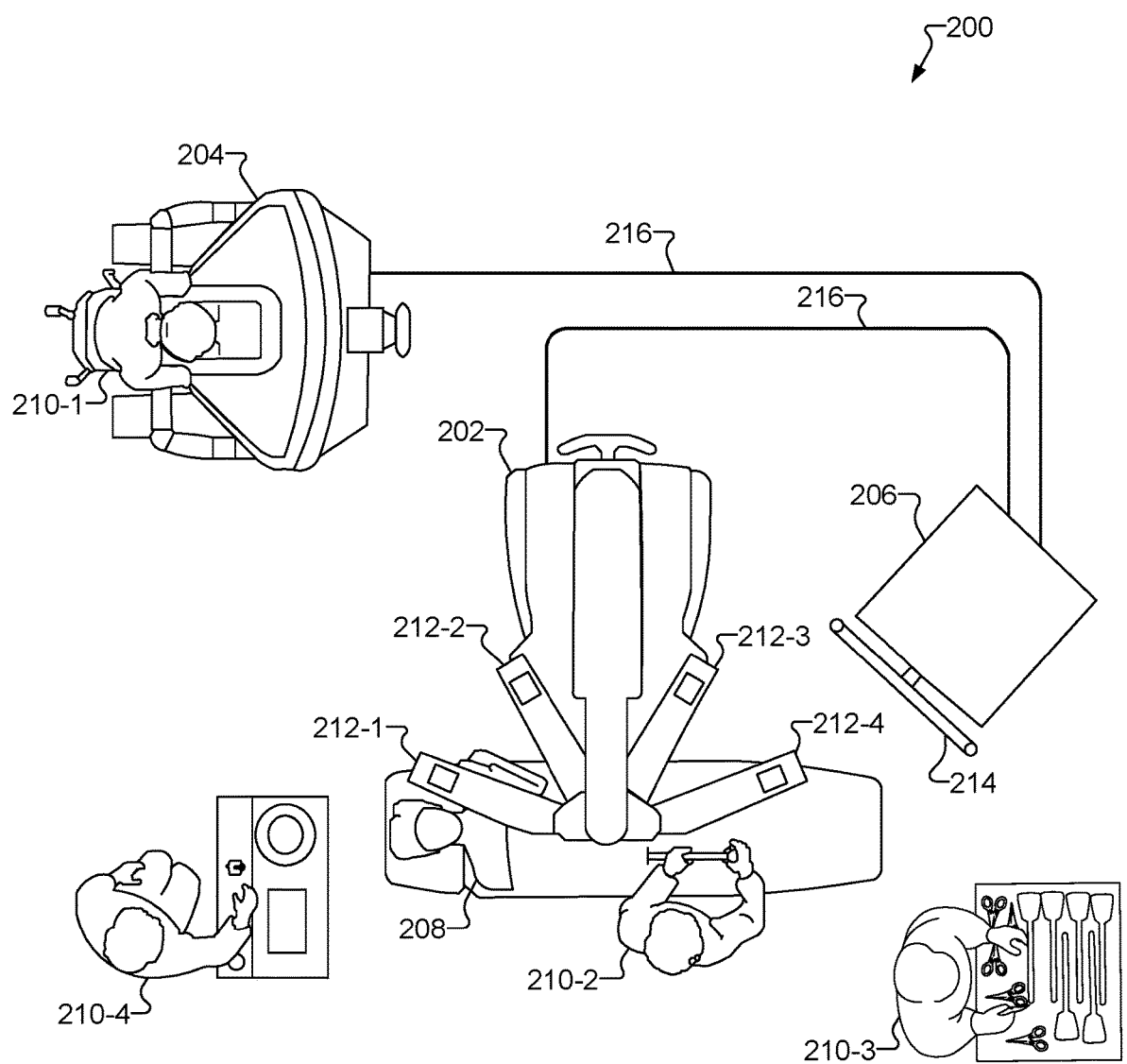
FIG. 2 illustrates an exemplary computer-assisted surgical system according to principles described herein.

FIG. 2 illustrates an exemplary computer-assisted surgical system ("surgical system 200"). As shown, surgical system 200 may include a manipulating system 202, a user control system 204 (also referred to herein as a surgeon console), and an auxiliary system 206 (also referred to herein as an auxiliary console) communicatively coupled one to another. Surgical system 200 may be utilized by a surgical team to perform a computer-assisted surgical procedure on a body of a patient 208. As shown, the surgical team may include a surgeon 210-1, an assistant 210-2, a nurse 210-3, and an anesthesiologist 210-4, all of whom may be collectively referred to as "surgical team members 210." Additional or alternative surgical team members may be present during a surgical session as may serve a particular implementation.

While FIG. 2 illustrates an ongoing minimally invasive surgical procedure, it will be understood that surgical system 200 may similarly be used to perform open surgical procedures or other types of surgical procedures that may similarly benefit from the accuracy and convenience of surgical system 200. Additionally, it will be understood that the surgical session throughout which surgical system 200 may be employed may not only include an operative procedural phase of a surgical procedure, as is illustrated in FIG. 2, but may also include preoperative, postoperative, and/or other suitable procedural phases of the surgical procedure.

As shown in FIG. 2, manipulating system 202 may include a plurality of manipulator arms 212 (e.g., manipulator arms 212-1 through 212-4) to which a plurality of surgical instruments and/or other tools (e.g., imaging devices such as an endoscope, an ultrasound tool, etc.) may be coupled. Each surgical instrument may be implemented by any suitable therapeutic instrument (e.g., a tool having tissue-interaction functions), diagnostic instrument, or the like that may be used for a computer-assisted surgical procedure on patient 208 (e.g., by being at least partially inserted into patient 208 and manipulated to perform a computer-assisted surgical procedure on patient 208). In some examples, one or more of the surgical instruments may include force-sensing and/or other sensing capabilities. In some examples, an imaging device may be implemented by an endoscopic device or another suitable imaging device such as an ultrasound module that is connected to or coupled with a surgical instrument. While manipulating system 202 is depicted and described herein as including four manipulator arms 212, it will be recognized that manipulating system 202 may include only a single manipulator arm 212 or any other number of manipulator arms as may serve a particular implementation.

Manipulator arms 212, as well as surgical instruments and/or imaging devices attached to manipulator arms 212, may include one or more displacement transducers, orientational sensors, and/or positional sensors used to generate raw (i.e., uncorrected) kinematics information. In some examples, system 100 and/or surgical system 200 may be configured to use the kinematics information to track (e.g., determine positions of) and/or control surgical instruments and/or imaging devices (as well as anything held by or connected to the instruments and/or imaging devices such as a retracted piece of tissue, a needle used for suturing or another such surgical tool, etc.).

User control system 204 may be configured to facilitate control by surgeon 210-1 of manipulator arms 212 and surgical instruments and/or imaging devices attached to manipulator arms 212. For example, surgeon 210-1 may interact with user control system 204 to remotely move or manipulate manipulator arms 212 and the instruments or devices attached thereto. To this end, user control system 204 may provide surgeon 210-1 with imagery of a surgical site associated with patient 208 as captured by an imaging device. In certain examples, user control system 204 may include a stereo viewer having two displays where stereoscopic images of a surgical site associated with patient 208 and generated by a stereoscopic imaging device may be viewed by surgeon 210-1. Captured imagery, as well as data or notifications generated by system 100, may be displayed by user control system 204 to facilitate surgeon 210-1 in performing one or more procedures with surgical instruments attached to manipulator arms 212.

To facilitate control of surgical instruments and imaging devices during the surgical procedure, user control system 204 may include a set of master controls. These master controls may be manipulated by surgeon 210-1 to control movement of instruments and/or imaging devices such as by utilizing robotic and/or teleoperation technology. The master controls may be configured to detect a wide variety of hand, wrist, and finger movements by surgeon 210-1. In this manner, surgeon 210-1 may intuitively perform a procedure using one or more surgical instruments and imaging devices.

Auxiliary system 206 may include one or more computing devices configured to perform primary processing operations of surgical system 200. In such configurations, the one or more computing devices included in auxiliary system 206 may control and/or coordinate operations performed by various other components (e.g., manipulating system 202 and user control system 204) of surgical system 200. For example, a computing device included in user control system 204 may transmit instructions to manipulating system 202 by way of the one or more computing devices included in auxiliary system 206. As another example, auxiliary system 206 may receive (e.g., from manipulating system 202) and may process image data representative of imagery captured by an imaging device.

In some examples, auxiliary system 206 may be configured to present visual content to surgical team members 210 who may not have access to the images provided to surgeon 210-1 at user control system 204. To this end, auxiliary system 206 may include a display monitor 214 configured to display captured imagery, one or more user interfaces, notifications or information generated by system 100, information associated with patient 208 and/or the surgical procedure, and/or any other visual content as may serve a particular implementation. In some examples, display monitor 214 may display extended reality images (e.g., augmented reality images, etc.) of the surgical site that includes live video capture together with augmentations such as textual and/or graphical content (e.g., anatomical models generated preoperatively, contextual information, etc.) concurrently displayed with the images. In some embodiments, display monitor 214 is implemented by a touchscreen display with which surgical team members 210 may interact (e.g., by way of touch gestures) to provide user input to surgical system 200.

Manipulating system 202, user control system 204, and auxiliary system 206 may be communicatively coupled one to another in any suitable manner. For example, as shown in FIG. 2, manipulating system 202, user control system 204, and auxiliary system 206 may be communicatively coupled by way of control lines 216, which may represent any wired or wireless communication link as may serve a particular implementation. To this end, manipulating system 202, user control system 204, and auxiliary system 206 may each include one or more wired or wireless communication interfaces, such as one or more local area network interfaces, Wi-Fi network interfaces, cellular interfaces, etc.

Figure 3:
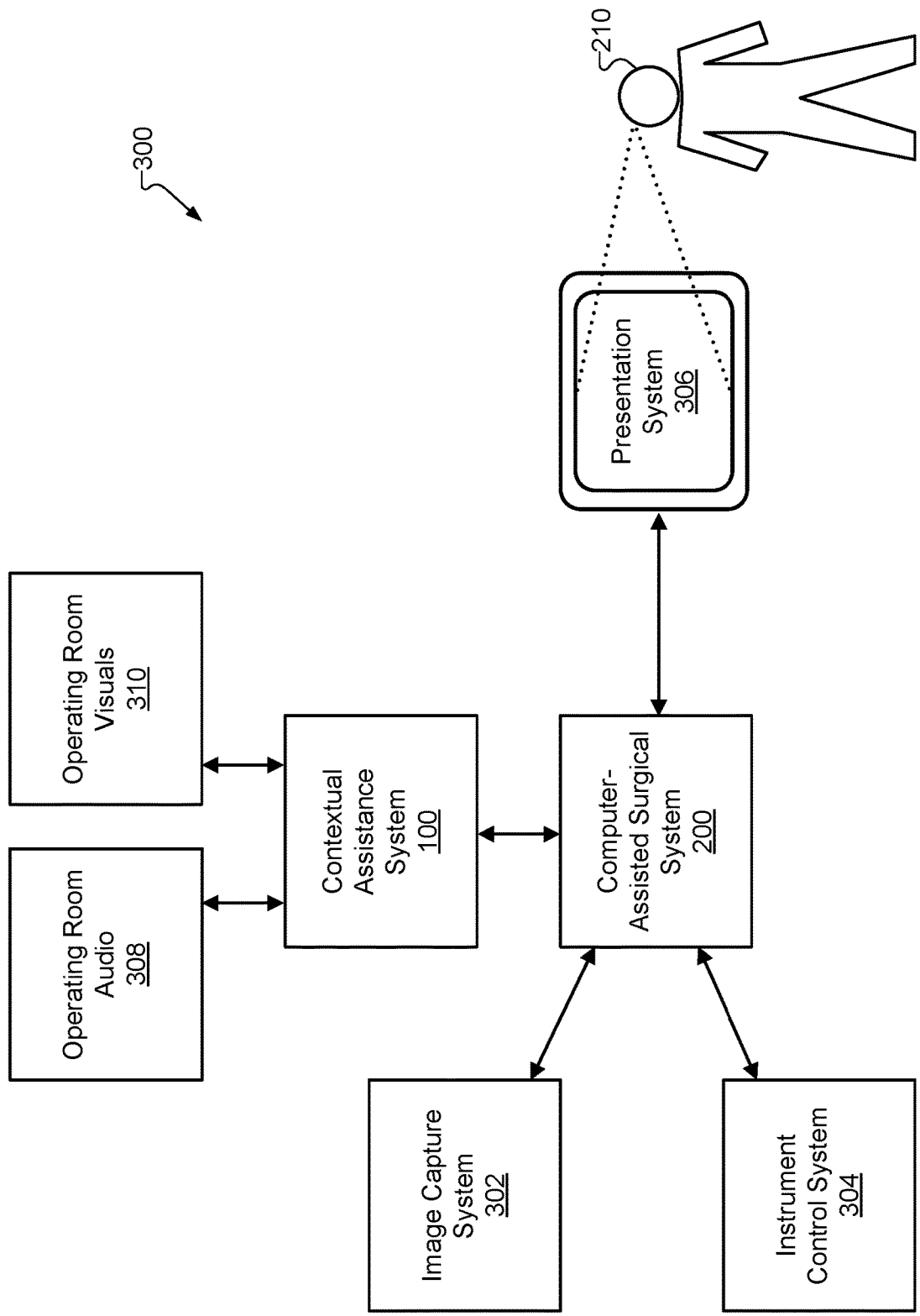
FIG. 3 illustrates an exemplary block diagram showing how the contextual assistance system of FIG. 1 may, along with other systems, integrate and/or interoperate with the computer-assisted surgical system of FIG. 2 according to principles described herein.

FIG. 3 illustrates an exemplary block diagram 300 showing how system 100 may, along with other systems, integrate and/or interoperate with surgical system 200. Specifically, as shown, block diagram 300 depicts an image capture system 302, an instrument control system 304, and a presentation system 306 that are integrated or coupled, together with system 100, with surgical system 200. Additionally, system 100 is further shown to receive data representative of operating room audio 308 and/or operating room visuals 310 from a suitable source such as microphones and/or cameras located in the operating room.

In various embodiments, system 100 may be implemented by or integrated into surgical system 200, while in other embodiments, system 100 may be separate from but communicatively coupled to surgical system 200. For example, system 100 may receive input from and provide output to surgical system 200 and/or may access imagery of a surgical site, information about the surgical site, and/or information about surgical system 200 from surgical system 200. System 100 may use this accessed imagery and/or information to perform any of the operations described herein to provide surgical assistance based on operational context of a surgical procedure. In a similar manner, image capture system 302, instrument control system 304, presentation system 306, any sensors or systems configured to capture and provide operating room audio 308 and operating room visuals 310, and/or any combination thereof may be implemented by (e.g. integrated into) surgical system 200 or, if separate from surgical system 200, may be communicatively coupled therewith and controlled by processing resources of surgical system 200. Each of elements 302 through 310 will now be described in more detail.

Image capture system 302 may include an endoscope or another suitable imaging device, as well as, in certain examples, computing resources configured to process data (e.g., image data, video data, depth data, metadata, etc.) captured by the imaging device and/or to generate and provide such data to system 100. For example, image capture system 302 may capture and generate a first version of an image that, when processed by system 100, will be augmented to form a second version of the image in which a depiction of a particular object is augmented in accordance with principles described herein. In certain examples, an imaging device included within image capture system 302 may be implemented as a stereoscopic imaging device (e.g., a stereoscopic endoscope) that includes stereoscopic imaging elements such as twin capture elements disposed at a preconfigured distance apart so as to provide image data configured to leverage the stereoscopic vision of the surgeon using the stereoscopic endoscope to view the surgical site.

In such implementations, system 100 may generate and provide depth data for the surgical site along with image data for the site. For example, system 100 may determine depth data for objects and imagery at the surgical site using a stereoscopic depth detection technique that employs the stereoscopic imaging elements of the stereoscopic imaging device. Such a technique may be performed by correlating surface points captured by each of the stereoscopic imaging elements from their respective vantage points, and triangulating (e.g., based on the known preconfigured distance between the vantage points of the two imaging elements) how far each of these surface points are from the imaging device. In this way, image capture system 302 may detect and provide, along with captured image data, depth data representative of the surgical site to system 100 (e.g., by way of surgical system 200). In certain examples, image capture system 302 may include a monoscopic imaging device rather than a stereoscopic imaging device. In these or other examples, depth detection techniques may be employed that operate on principles such as time-of-flight depth detection or the like.

Instrument control system 304 may include or be implemented by any suitable surgical instrumentation and/or processing or control resources used to facilitate use of the instrumentation as may serve a particular implementation. For instance, in some examples, instrument control system may include one or more tissue manipulation instruments (e.g., cutting instruments, grasping instruments, etc.) configured for use during a surgical procedure to manipulate tissue as may serve a particular surgical procedure. In some implementations, instrument control system 304 may include force sensors such as displacement transducers, orientational sensors, and/or positional sensors that are used to generate raw kinematics data for use in any of the ways described herein.

Upon augmenting a depiction of a particular object within a version of an image captured by image capture system 302, system 100 may generate and display the augmented image itself, or may provide the augmented image for display by another system. For instance, presentation system 306 may represent one example of such a system to which system 100 may provide an augmented version of an image. Presentation system 306 may include or be implemented by any suitable display screen and/or processing resources used to present information to a user such as a surgical team member 210 (e.g., surgeon 210-1 or any other member of the team performing the surgical procedure). In some examples, system 100 may be configured to present information by way of presentation system 306. For example, system 100 may provide, during the surgical procedure, an augmented version of an image to presentation system 306 to be presented to a surgical team member 210.

As will be described in more detail below, various techniques may be employed for identifying an operational context of an ongoing surgical procedure including which procedural phase of the procedure is currently being performed. In some examples, operating room audio 308 and/or operating room visuals 310 may be used to facilitate system 100 in identifying the operational context. Accordingly, microphones or other such audio capture sensors placed in an operating room or other area where the surgical procedure is being performed may be configured to provide operating room audio 308 to facilitate the identification of the operational context of the surgical procedure. Additionally or alternatively, video cameras or other such visual capture sensors mounted in the operating room or other area where the surgical procedure is being performed may be configured to provide operating room visuals 310 to further facilitate the identification of the operational context of the surgical procedure.

As used herein, a surgical procedure may include any medical procedure, including any diagnostic, therapeutic, or treatment procedure in which manual and/or instrumental techniques are used on a body of a patient or other subject (e.g., a cadaver, an animal, a surgical training fixture, etc.) to investigate or treat a physical condition. A surgical procedure may be performed at a surgical site that will be understood to include any volumetric space associated with the surgical procedure. For example, the surgical site may include any part or parts of a body of a patient or other subject of the surgery in a space associated with the surgical procedure. The surgical site may, in certain examples, be entirely disposed within the body and may include a space within the body near where a surgical procedure is being performed. For example, for a minimally invasive surgical procedure being performed on tissue internal to a patient, the surgical site may include the surface tissue, anatomy underlying the surface tissue, as well as space around the tissue where, for example, surgical instruments being used to manipulate the tissue to thereby perform the procedure are located. In other examples, the surgical site may be at least partially located external to the patient. For instance, for an open surgical procedure being performed on a patient, part of the surgical site may be internal to the patient while another part of the surgical site (e.g., a space around the tissue where one or more surgical instruments may be located) may be external to the patient.

Figure 4:
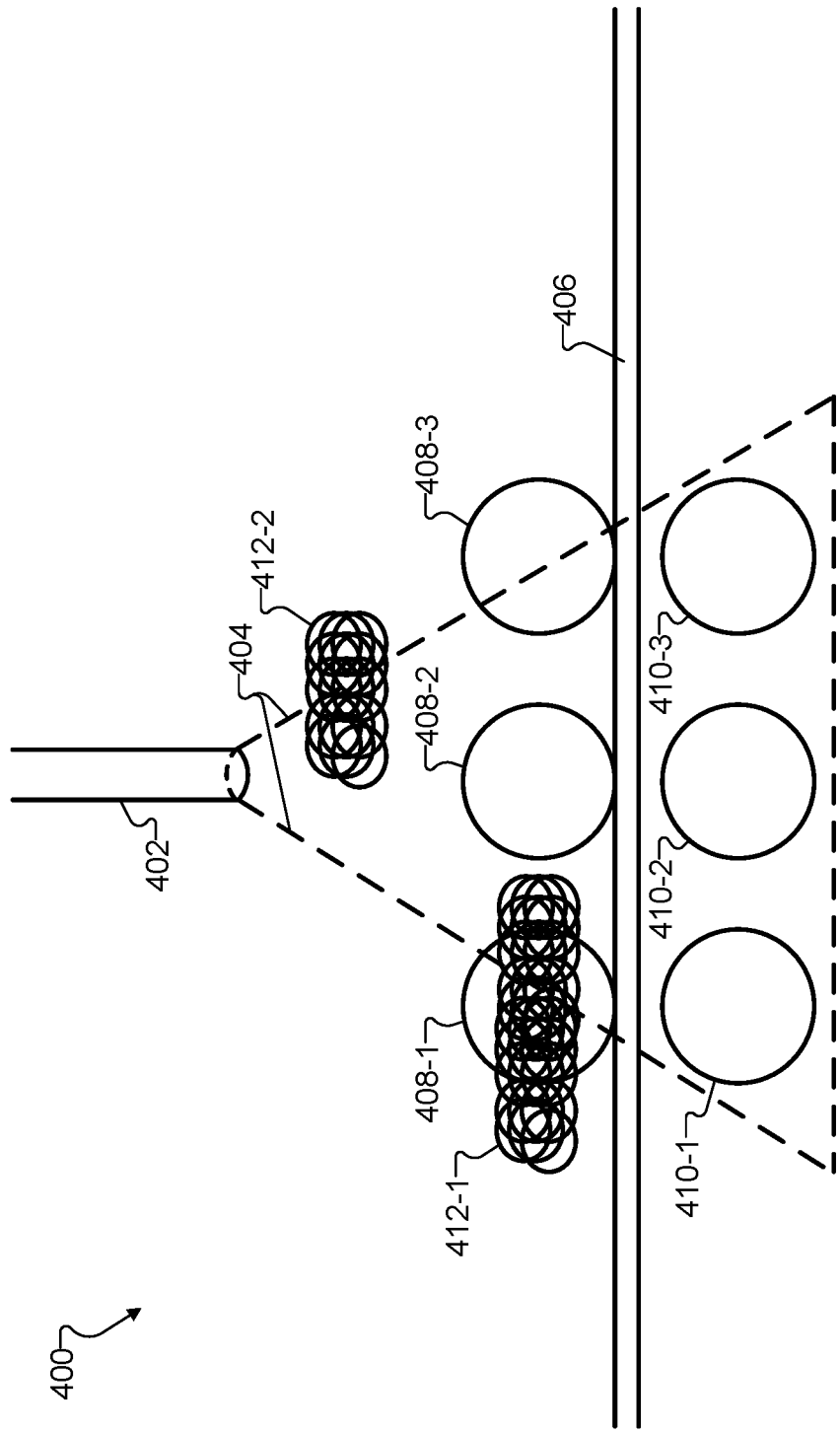
FIG. 4 illustrates an exemplary surgical site at which an imaging device captures images depicting various objects according to principles described herein.

FIG. 4 shows an exemplary surgical site 400 at which an imaging device 402 captures images depicting various objects according to principles described herein. In FIG. 4, surgical site 400 will be understood to be located inside a body (e.g., a body of a patient or the like), the outside of which is not explicitly shown. Imaging device 402 may be implemented by an endoscope (e.g., a stereoscopic endoscope) associated with an image capture system such as image capture system 302 described above. As shown, imaging device 402 may capture imagery at surgical site 400 in accordance with a field of view 404 that covers different objects and imagery depending on the orientation of imaging device 402.

Specifically, as illustrated, certain aspects of surgical site 400 are shown to be included within field of view 404 while other aspects of surgical site 400 are shown to fall outside of field of view 404. For example, a certain portion of a tissue surface 406 (e.g., the surface of a particular organ or other anatomical structure) is shown to be included within field of view 404 while imaging device 402 is oriented in the configuration shown in FIG. 4, while other portions of tissue surface 406 present at surgical site 400 are shown to be outside of field of view 404 unless the orientation of imaging device 402 were to be changed (e.g., by moving or reorienting imaging device 402).

A plurality of surface objects 408 (e.g., surface objects 408-1 through 408-3) are depicted above tissue surface 406 in FIG. 4, while a plurality of subsurface objects 410 (e.g., subsurface objects 410-1 through 410-3) are depicted below tissue surface 406. While each of these objects 408 and 410 are illustrated as simple geometric circles in FIG. 4 for purposes of illustration, it will be understood that objects 408 and 410 may each implement or include any suitable type of anatomical, mechanical, or other object as may be present at surgical site 400. For example, one or more of surface objects 408 may represent surgical instruments such as those described above, or objects being carried or manipulated by such instruments. A needle and thread object used for suturing or another such tool may be carried by one such surgical instrument, for instance, and may be represented by one of surface objects 408. A resected piece of tissue or other anatomical structure may also be carried or manipulated by a surgical instrument in certain examples and may be represented by another one of surface objects 408, Another example of a surface object 408 may be an ultrasound probe that is placed on tissue surface 406 to perform imaging of subsurface objects 410, which may represent various anatomical structures (e.g., the internal vasculature and/or other anatomy within an organ) beneath tissue surface 406.

As shown, portions of objects 408-1 and 408-3, as well as an entirety of object 408-2, are included within field of view 404 and will thus be understood to be captured for images generated by imaging device 402 in the illustrated configuration of imaging device 402. It will be understood that portions of objects 408-1 and 408-3 that fall outside of field of view 404 (as well as, possibly, other objects not explicitly shown) are not currently captured by imaging device 402 even though they are present at surgical site 400.

While subsurface objects 410 are shown to be included geometrically within field of view 404, it will be understood that these objects may not be depicted in images captured by imaging device 402 if imaging device 402 is implemented as an endoscopic imaging device that cannot "see through" tissue surface 406. However, as will be described in more detail below, 3D models or other representations of such subsurface objects may be overlaid or otherwise imposed on images captured by imaging device 402 as augmentations added by system 100. When such augmentations are aligned properly, an augmented version of images captured by imaging device 402 may depict simulated representations of subsurface objects 410 alongside captured representations of surface objects 408.

Figure 5A:
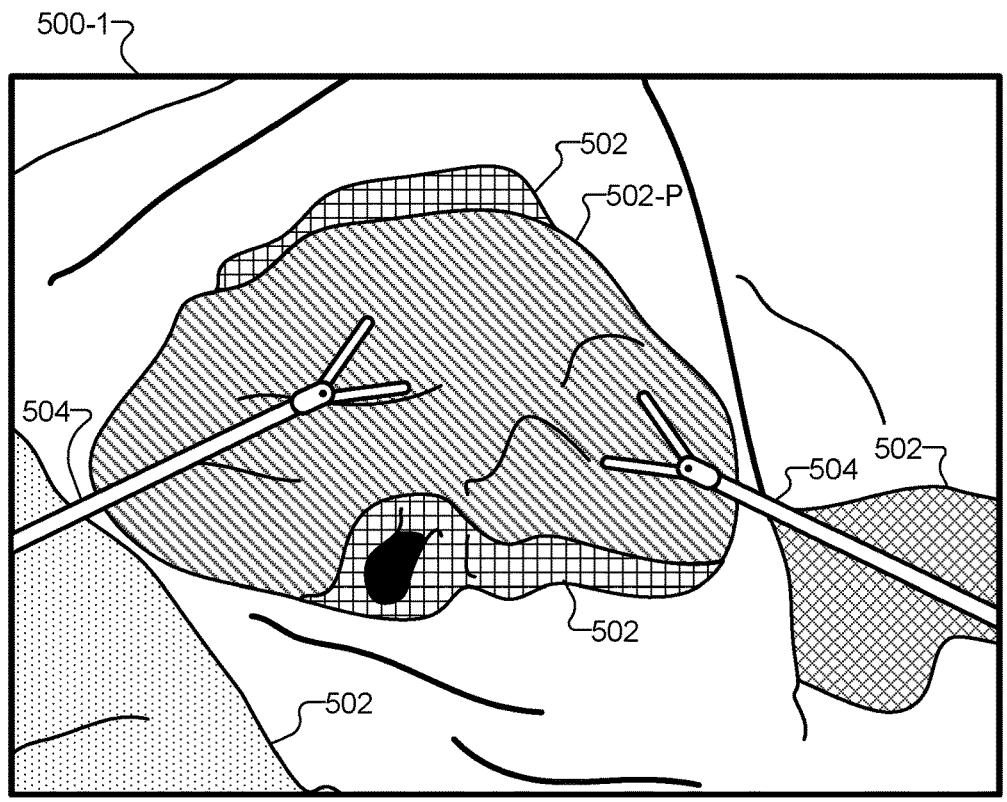
FIGS. 5A and 5B illustrate various aspects of an exemplary way of augmenting a depiction of an object at a surgical site according to principles described herein.
Figure 5B:
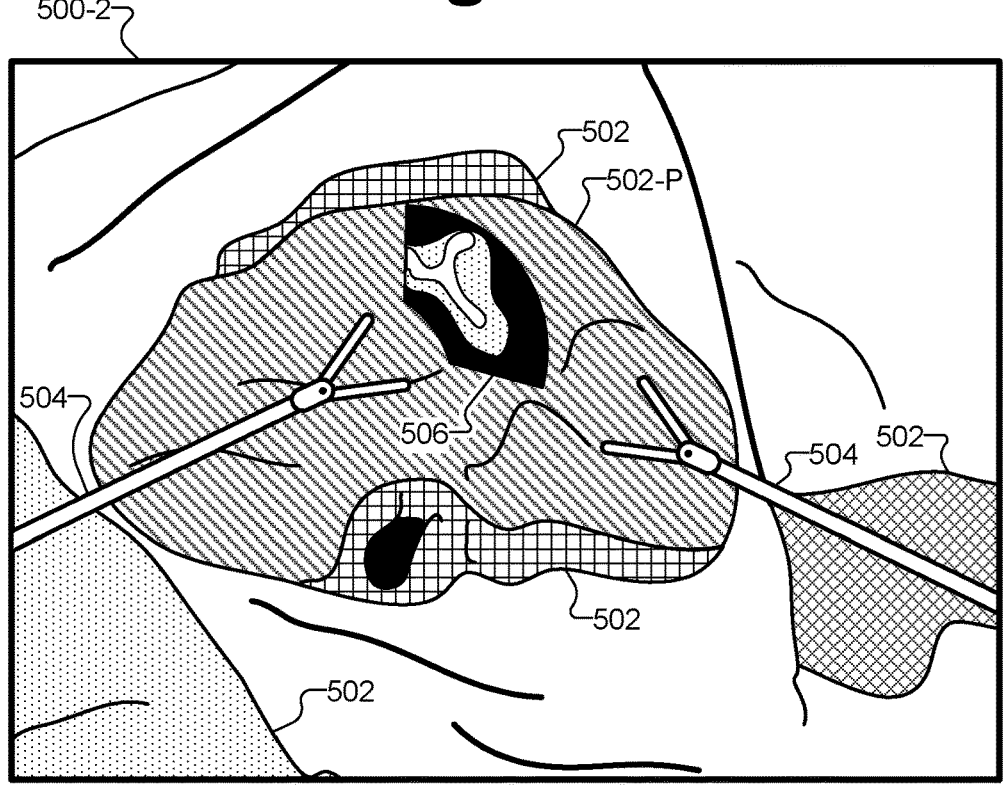

To illustrate, FIGS. 5A and 5B illustrate various aspects of one exemplary way of augmenting a depiction of an object at a surgical site according to principles described herein. Specifically, FIG. 5A shows an image 500-1 that will be understood to be a first version of a particular image captured by an imaging device such as imaging device 402, while FIG. 5B shows an image 500-2 that will be understood to be a second version of the same particular image after the image has been augmented by system 100.

In each of images 500-1 and 500-2 (collectively referred to herein as images 500), a surgical site including various surface objects is shown. Specifically, various anatomical structures 502 are shown (some of which are explicitly labeled while others are not) together with two surgical instruments 504 that are configured to manipulate tissue at the surgical site during a surgical procedure. In this example, system 100 will be understood to have detected a particular object present at the surgical site depicted by image 500-1. For example, anatomical structure 502-P may be identified as a particular organ (e.g., a kidney, etc.) upon which a particular procedural phase of the surgical procedure (e.g., a partial nephrectomy) is to be performed. Accordingly, based on operational context such as that the particular procedural phase of the surgical procedure is ongoing, system 100 may perform the augmenting of the depiction of the particular object (i.e., anatomical structure 502-P in this example) within the second version of the image (i.e., image 500-2). Specifically, for example, system 100 may display within the second version of the image (e.g., in addition to the depiction of all of objects 502 and instruments 504, including anatomical structure 502-P), a representation 506 of subsurface objects and imagery present at the surgical site but not depicted in the first version of the image (i.e., image 500-1).

As shown, representation 506 of the subsurface object may be based on a predefined model of the subsurface object generated using preoperative scan data captured prior to the surgical procedure. For example, if anatomical structure 502-P is a kidney and the surgical procedure being performed is a partial nephrectomy, representation 506 may represent a portion of a 3D model of the kidney that is generated prior to the surgical procedure based on preoperative imaging (e.g., computed tomography ("CT") or magnetic resonance imaging ("MRI") scanning, etc.) of the kidney. Representation 506 may be displayed, in whole or in part, as an augmentation on image 500-2 in order to facilitate the particular procedural phase of the surgical procedure that is being performed.

In this example, the operational context identified by system 100 has been described as a particular procedural phase of the surgical procedure being performed, while the augmentation made by system 100 to image 500-2 has been described as displaying representation 506 of a 3D model generated based on preoperative image. It will be understood, however, that in other examples, other types of operational context may be identified and/or other types of augmentations to image 500-2 may be imposed in addition or as an alternative to those illustrated in FIG. 5B.

For example, one aspect of the operational context that may be identified by system 100, and upon which the displaying of representation 506 may be based, is whether a suitable registration of the 3D model has been achieved with the imagery being captured, whether obscurants such as fat or blood are present and would tend to make the representation difficult to see, or other such contextual aspects. As another example, the portion of a 3D model shown in representation 506 (in an example in which the entire 3D model is not presented at once) may be determined by operational context including what procedural phase of the surgical procedure is ongoing. For instance, if arterial clamping is being performed, an arterial portion of the 3D model may be presented while other portions of the 3D model may not be shown. In still other examples, textual information, non-model graphics, or other information may be imposed on the image as an augmentation instead of or in addition to representation 506 of the 3D model shown in FIG. 5B.

In addition or as an alternative to augmenting an image in ways such as those described in relation to FIGS. 5A and 5B, system 100 may also augment a captured image to provide surgical assistance based on operational context in other ways. For instance, certain augmentations implemented by system 100 may relate to highlighting or emphasizing important, occluded, or obscured objects at a surgical site that might otherwise not be clearly displayed in an image or depicted with an optimal amount of emphasis. Such augmentations may involve any new virtual elements (e.g., transparency, color, rendering style change, etc.) being added to the second version of the image in certain examples, while in other examples, such augmentations may not involve any virtual element, but, rather, may bring attention or clarity to the objects in other ways.

As one example, system 100 may augment a depiction of a particular object such as an instrument or a tool based on an identification of operational context indicating that the instrument or tool is related to tasks being performed as part of the surgical procedure. For example, if a needle and thread are used during a suturing phase of a surgical procedure and system 100 determines that the suturing phase is occurring, system 100 may augment the depiction of the needle and/or thread (as well as, in certain examples, a surgical instrument holding the needle and performing the stitching) within the second version of the image by modifying (from the first version of the image) a depiction of the needle and/or thread so as to highlight or otherwise emphasize the depiction of the needle and/or thread in the second version of the image. For example, system 100 may implement a glowing halo around the needle and thread, impose a tail that briefly follows the needle and thread when moved around within the scene, outline the edges of the needle and thread with bright or different colored lines to cause the objects to stand out, or otherwise highlight or emphasize the needle and thread in any manner as may serve a particular implementation.

As another example, system 100 may augment a depiction of one or more objects based on an identification of operational context indicating that obscurants are present at the surgical site that may make the objects difficult to see. Returning to FIG. 4, this situation is illustrated by various obscurants 412 (e.g., obscurant 412-1 and 412-2) that are at least partially included within field of view 404 such that they obscure or totally occlude certain objects 408 from being viewed from the perspective of imaging device 402.

Obscurants 412 may represent any of the obscurants that have been mentioned herein or any other objects, substances, liquids, gases, or other materials that may at least partially obscure or diminish a view of an object from a vantage point of an imaging device attempting to capture that view. For example, as shown in FIG. 4, object 408-1 may be obscured by obscurant 412-1, which may represent blood, fat, or another substance present at surgical site 400 and that surrounds or covers object 408-1. As another example, objects 408-2 and 408-3 are shown to each be at least partially obscured or occluded by obscurant 412-2, which may represent smoke (e.g., created during a cauterization process or the like) or another such substance, by an inactive instrument idly stationed above the objects 408, or by any other object or material that at least partially blocks the view that imaging device 402 has of objects 408 at surgical site 400.

Accordingly, in these types of examples, system 100 may identify the operational context upon which the augmenting will be based by detecting that an obscurant present at the surgical site is at least partially obscuring a view of a particular object (e.g., one of objects 408) as depicted by the first version of the image. For example, as mentioned, the obscurant may include at least one of blood, fat, or smoke. System 100 may then augment the depiction of the particular object within the second version of the image by displaying (e.g., within the second version of the image in place of the depiction of the particular object captured within the first version of the image), a representation of the particular object that is based on a predefined model of the particular object. For example, if the particular object is a surgical instrument, the predefined model used may be a computer-aided design ("CAD") model for the surgical instrument that is available to system 100, or, if the particular object is an anatomical structure, the predefined model used may be a 3D model such as described above that is generated based on preoperative imaging (e.g., CT scanning, MRI scanning, etc.).

Figure 6A:
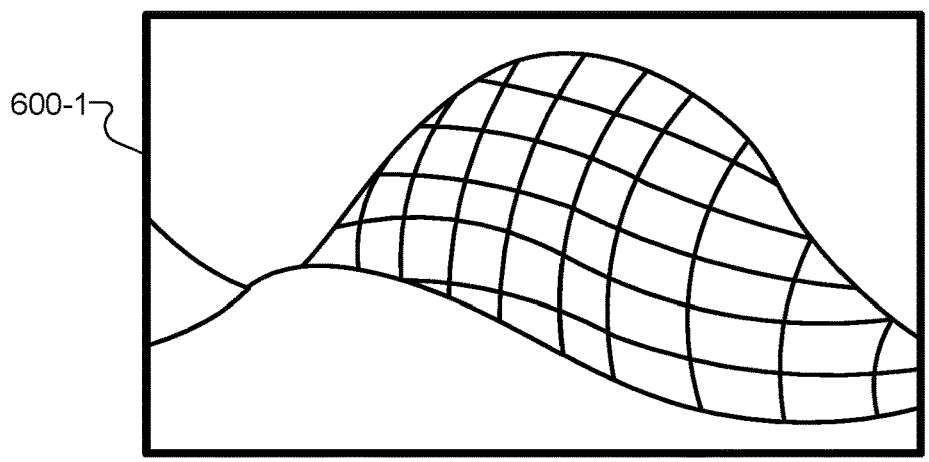
FIGS. 6A through 6C illustrate various aspects of an exemplary obscurant that at least partially obscures a view of an anatomical structure and an exemplary way of augmenting a depiction of the anatomical structure according to principles described herein.
Figure 6B:
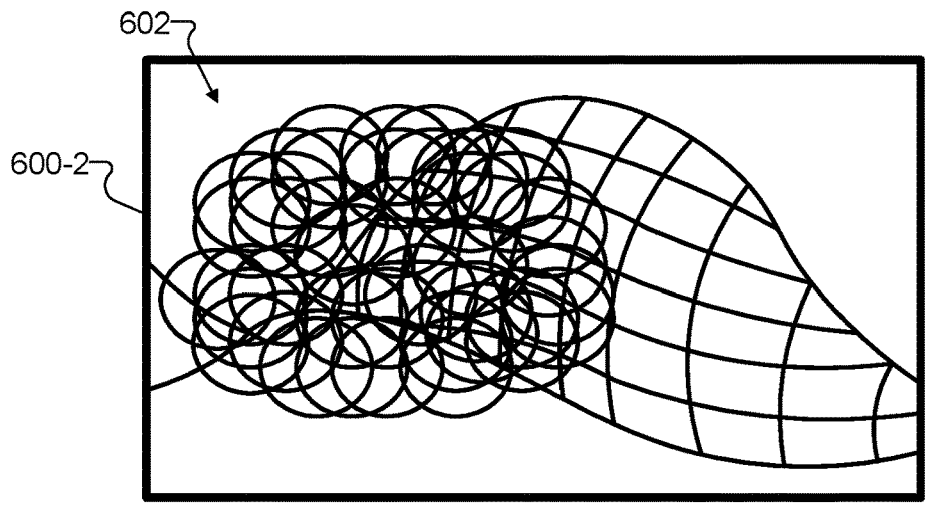
Figure 6C:
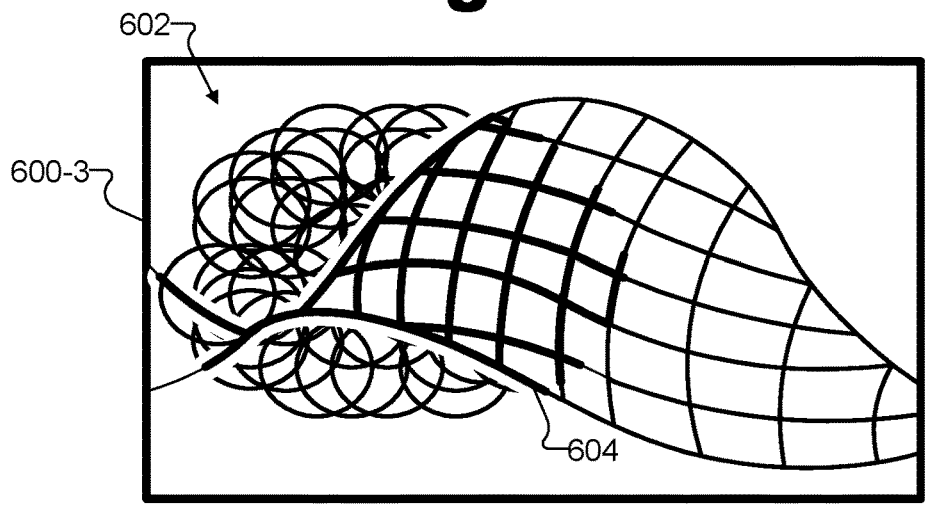
Figure 7A:
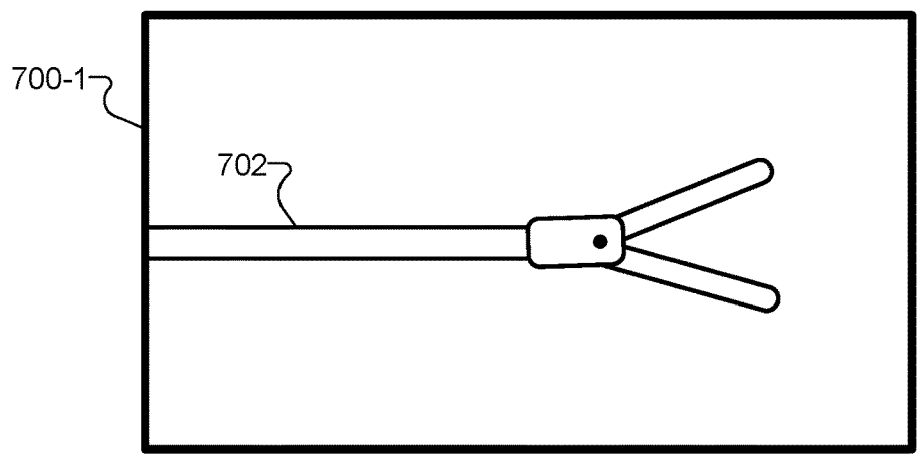
FIGS. 7A through 7C illustrate various aspects of an exemplary obscurant that at least partially obscures a view of an instrument object and an exemplary way of augmenting a depiction of the instrument object according to principles described herein.
Figure 7B:
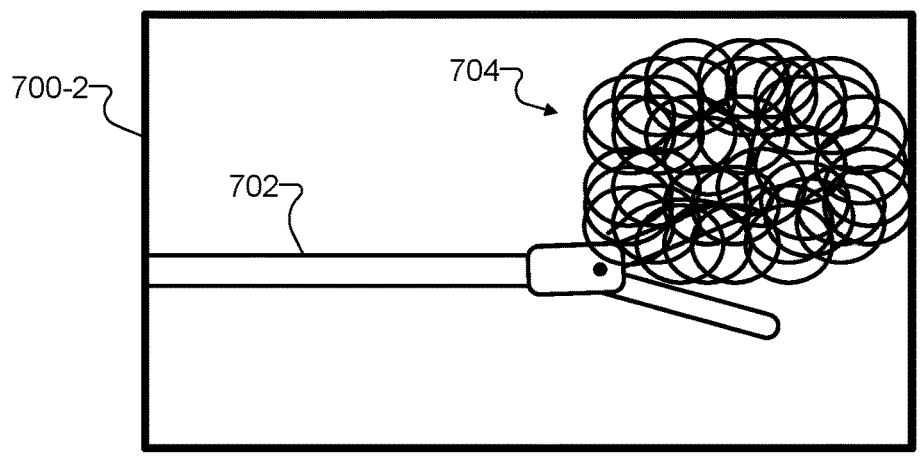
Figure 7C:
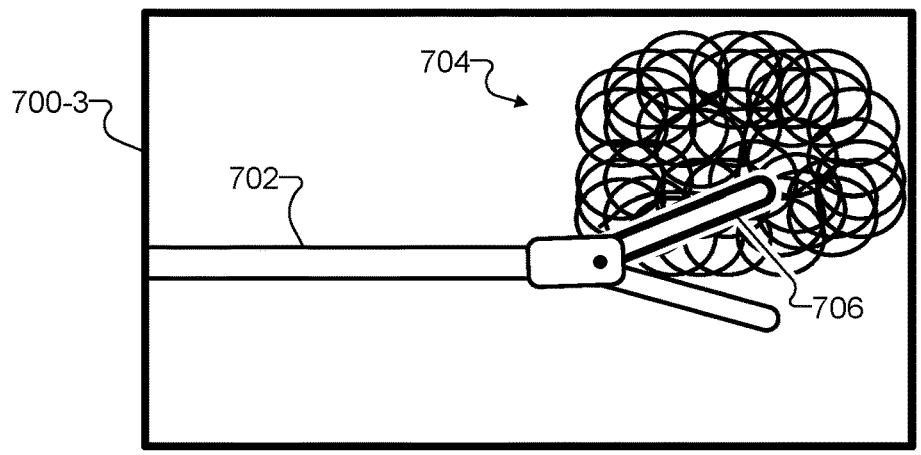

To illustrate both of these types of exemplary augmentations, FIGS. 6A through 6C illustrate various aspects of an exemplary obscurant that at least partially obscures a view of an anatomical structure and an exemplary way of augmenting a depiction of the anatomical structure, while FIGS. 7A through 7C illustrate various aspects of another exemplary obscurant that at least partially obscures a view of a surgical instrument and an exemplary way of augmenting a depiction of the instrument.

More specifically, FIG. 6A shows an image 600-1 depicting a surgical site without any obscurant present. For example, the anatomical imagery shown in FIG. 6A may represent a view of a surgical site prior to a cauterizing event that produces smoke at the site, or prior to another event that release blood or another such obscurant. As depicted in image 600-1, objects and imagery at the surgical site may be seen and captured clearly in this example.

Such is not the case, however, in the example of FIG. 6B. FIG. 6B shows an image 600-2 that depicts the same surgical site when an obscurant 602 (e.g., smoke, blood, fat, etc.) is present at the site to at least partially block a view of certain anatomical structures and objects present at the site. Image 600-2 will be understood to be a raw version of a particular image that is captured by an imaging device (e.g., imaging device 402) at a moment in time when obscurant 602 is present, such as shortly after a cauterizing operation is performed or after another such event.

FIG. 6C shows an image 600-3 that will be understood to be a processed version (i.e., an augmented version) of the same particular image as image 600-2 in which obscurant 602 is present at the surgical site. However, rather than being a raw image captured by an imaging device (as is the case with image 600-2), image 600-3 represents an augmented image that has been processed and generated by system 100 in accordance with principles described herein. As shown in image 600-3, obscurant 602 is still present at the surgical site. However, whereas obscurant 602 significantly interfered with a view of the depicted anatomical structure in image 600-2, an augmentation 604 allows the anatomical structure to be much more readily viewable in image 600-3 to thereby assist the surgical team as the surgical procedure is performed. Specifically, as shown, augmentation 604 looks very similar or identical to the portion of the anatomy that is obscured and is overlaid on the raw image so as to mitigate the effect that obscurant 602 has on visibility of the structure.

In a similar example depicted in FIGS. 7A-7C, another type of object is shown to illustrate similar principles as described above in relation to the anatomical structure objects of the example of FIGS. 6A-6C. Specifically, FIG. 7A shows an image 700-1 depicting a surgical instrument 702 at a surgical site that does not have any obscurant present. For example, the depiction of surgical instrument 702 shown in FIG. 7A may represent a view at the surgical site prior to a cauterizing event that produces smoke at the site, or prior to another event that release blood or another such obscurant.

While surgical instrument 702 is clearly depicted in image 700-1, such is not the case in the example of FIG. 7B. FIG. 7B shows an image 700-2 that depicts the same surgical instrument when an obscurant 704 (e.g., smoke, blood, fat, etc.) is present to at least partially block a view of surgical instrument 702. Image 700-2 will be understood to be a raw version of a particular image that is captured by an imaging device (e.g., imaging device 402) at a moment in time when obscurant 704 is present, such as shortly after a cauterizing operation is performed, during a task where tissue covered by fat is being manipulated, or the like.

FIG. 7C shows an image 700-3 that will be understood to be a processed version (i.e., an augmented version) of the same particular image as image 700-2 in which obscurant 704 is present. However, rather than being a raw image captured by an imaging device (as is the case with image 700-2), image 700-3 represents an augmented image that has been processed and generated by system 100 in accordance with principles described herein. As shown in image 700-3, obscurant 704 continues to be present around surgical instrument 702. However, whereas obscurant 704 significantly interfered with a view of the surgical instrument 702 in image 700-2, an augmentation 706 allows surgical instrument 702 to be much more readily viewable in image 700-3 to thereby assist the surgical team as the surgical procedure is performed. Specifically, as shown, augmentation 706 looks very similar or identical to the portion of surgical instrument 702 that is obscured and is overlaid on the raw image so as to mitigate the effect that obscurant 704 has on visibility of surgical instrument 702.

In the examples of both FIGS. 6A-6C and 7A-7C, system 100 may be configured to perform the augmenting of the depiction of the particular object within the augmented version of the image in any manner as may serve a particular implementation. In one implementation, for instance, system 100 may begin by accessing a model that is available for the particular object that is to be augmented. For example, for the anatomical structure of FIGS. 6A-6C, system 100 may access a preoperative model of the anatomy that has been generated based on preoperative scanning or the like, while, for surgical instrument 702 of FIGS. 7A-7C, system 100 may access a CAD model of surgical instrument 702 that is made available when surgical instrument 702 is purchased or deployed. Next, system 100 may determine which portion of the particular object is to be augmented (unless, as in certain examples, the entire object is to be augmented rather than only a portion such as illustrated in these examples). System 100 may then rely on computer vision cues, kinematic data, machine learning, and/or other factors to determine the relative positions of the particular object to be augmented and the imaging device capturing the imagery. For example, computer vision and/or kinematic data may be used to determine where surgical instrument 702 is located with respect to the imaging device capturing image 700-2 and its field of view. Similarly, computer vision and/or kinematic data may be used to determine where a particular anatomical structure is located with respect to the image device and its field of view for image 600-2. Once these locations have been determined and a portion of the model has been identified, system 100 may overlay the portion of the model appropriately onto the raw image (e.g., image 600-2 or 700-2) in order to generate the augmented image (e.g., image 600-3 or 700-3) to be provided for presentation to the surgical team.

Additionally, in each of these and other examples, system 100 may be configured to perform the detecting that the particular object is present at the surgical site and depicted by a captured image in any suitable manner. As one example, for certain implementations and/or particular objects, system 100 may detect that the particular object is present at the surgical site by performing operations including 1) analyzing, using a computer-vision-based object recognition technology, the raw version of the image, and 2) determining, based on the analysis of the raw version of the image using the computer-vision-based object recognition technology, that the particular object is present at the surgical site depicted by the raw version of the image. In this example, any suitable object recognition technology may rely on computer vision to identify objects within the raw image as may serve a particular implementation. For instance, system 100 may search for and identify various features of objects depicted in the raw image and may use artificial intelligence technologies (e.g., machine learning trained on previous images, etc.) to match a combination of such features with known objects included in a database of objects likely to be present at the surgical site.

As another example, system 100 may detect that the particular object is present at the surgical site by performing operations including 1) accessing procedural data indicating that the particular object is held by a particular manipulator arm controlled by a computer-assisted surgical system, 2) accessing kinematic data indicative of a pose of the manipulator arm with respect to an image capture device capturing the raw version of the image, and 3) determining, based on the procedural data and the kinematic data, that the particular object is present at the surgical site depicted by the raw version of the image. In this example, the procedural data may be accessed from any suitable source (e.g., data maintained by system 100 or surgical system 200 that tracks what instruments and tools are being used at each particular stage of the surgical procedure, etc.) or may be automatically determined in real time by system 100. For instance, system 100 may access this procedural data by accessing operating room visual data 310 and analyzing the data to determine that a new tool or instrument is connected to the particular manipulating arm. System 100 may then use kinematic data provided by instrument control system 304 to determine that the manipulator arm is positioned such that the instrument or tool and any objects associated therewith (e.g., a needle held by the instrument or the like) are present at a location within the field of view of the imaging device such that the instrument or tool is determined to be depicted by images captured by the imaging device. One advantage of this technique for detecting that the particular object is present is that computer vision not need to be relied on (or relied on to the same extent as with a computer-vision-based object recognition technology), such that system 100 may be able to detect objects that are occluded or obscured during the surgical procedure by obscurants such as fat or smoke.

In some examples, a combination of both a computer-vision-based object recognition technology and a kinematic-based approach such as have been described may be employed to detect the particular object. In still other examples, other suitable approaches and technologies may be used to detect that the particular object is present at the surgical site and depicted within the raw image. Additionally, it will be understood that, in certain examples, system 100 may detect particular objects at least partially based on a determination of the current procedural phase (e.g., system 100 may search for a needle if the current procedural phase is a suturing phase, etc.) or may otherwise operate with a knowledge that the particular objects (e.g., vasculature, etc.) are present without any explicit detection of such. For example, system 100 may determine, at a particular time during the surgical procedure, that the surgical procedure is in a particular procedural phase of a plurality of predefined procedural phases that are planned to be performed as part of the surgical procedure, and may detect that the particular object is present at the surgical site at or after the particular time in response to the determining that the surgical procedure is in the particular procedural phase. Conversely, in other examples, the detection of a particular object may serve as a trigger or clue to help system 100 identify which procedural phase is ongoing (e.g., system 100 may identify a needle and, based on that identification, may determine that a suturing phase is ongoing, etc.).

As has been mentioned, another task that system 100 may perform while providing surgical assistance to users of surgical system 200 is to identify the operational context. As has been described, the operational context identified and acted on by system 100 may include any of various types of circumstances, conditions, events, or other such aspects of the surgical procedure. As with detecting a particular object present at the surgical site and augmenting a depiction of that object as described in detail above, the identifying of the operational context may also be performed in any manner as may serve a particular implementation.

As one example, system 100 may identify the operational context of a surgical procedure by accessing any of various types of procedural data and determining, based on the procedural data, that the surgical procedure is in a particular procedural phase of a plurality of predefined procedural phases that are planned to be performed as part of the surgical procedure. The procedural data accessed by system 100 for use in determining the procedural phase of the surgical procedure may refer to any type of data from any of various data sources that may help system 100 to identify which procedural phase is ongoing at a particular time.

For example, such procedural data may be received from surgical system 200 and may be representative of a surgical instrument currently employed in the performance of the surgical procedure, a pose of the surgical instrument during the surgical procedure (e.g., based on tracked kinematic data or the like), or other such information known to surgical system 200 and relevant to which instruments and tools are in use at the particular moment in question. As another example, such procedural data may include audio content recorded in the operating room during the surgical procedure (e.g., operating room audio 308) and may be accessed from a microphone or other sound capture system communicatively coupled to system 100. Similarly, procedural data may include image content (e.g., video data, etc.) recorded in the operating room during the surgical procedure (e.g., operating room visuals 310) and may be accessed from a video camera posted in the operating room. In yet other examples, procedural data may be direct user input data provided by a member of the surgical team performing the surgical procedure and directly indicative of which procedural phase is ongoing or other data from which the procedural phase may be derived. All of these types of procedural data that have been described will be understood to be examples only, and other forms of procedural data from other sources not explicitly described herein may also serve in certain implementations to further help system 100 identify which procedural phase of the surgical procedure is ongoing at a particular moment in time.

Based on any of these types of procedural data (or any combination thereof), system 100 may identify the procedural phase. In some examples, artificial intelligence technologies such as machine learning techniques may be employed to identify the procedural phase based on the procedural data in accordance with previously-performed surgical procedures used to train the artificial intelligence. In some examples, system 100 may also use cues such as timing and/or which instruments are being used, since each of these factors may be preplanned or identifiable using machine learning or other techniques. Additionally, the surgeon or another surgical team member may indicate manually to the system when a current procedural phase is complete and/or when a new procedural phase is commencing. In any of these or other suitable ways, system 100 may determine the procedural phase and/or otherwise identify the operational context of a particular surgical procedure.

Figure 8:
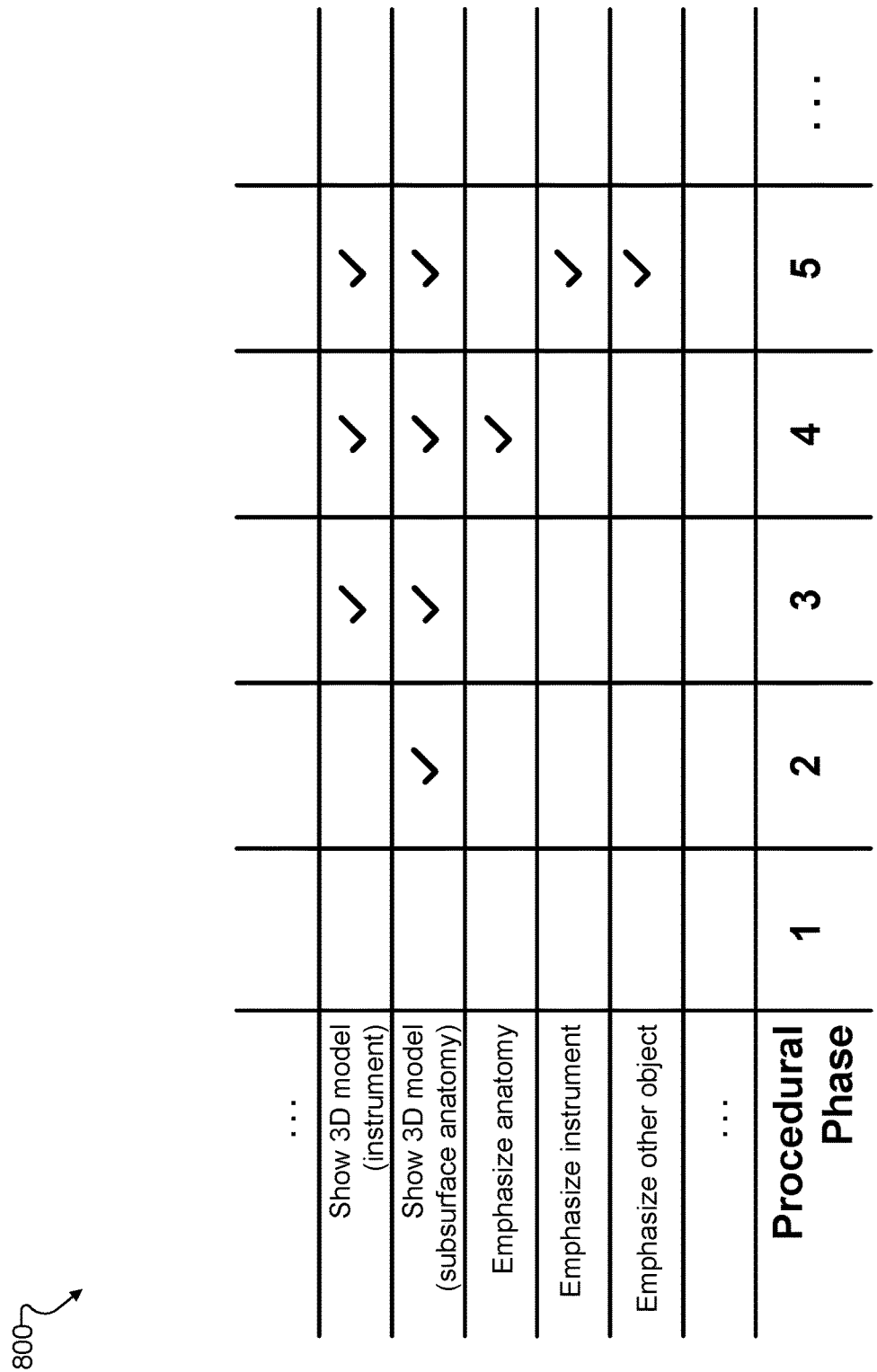
FIG. 8 illustrates exemplary aspects of a predefined plan for a surgical procedure according to principles described herein.

FIG. 8 illustrates exemplary aspects of a predefined plan for a surgical procedure. Specifically, FIG. 8 shows a plan 800 that includes a chart correlating various potential augmentations listed in the left column with various procedural phases (i.e., procedural phases labeled 1 through 5) laid out along the bottom row. The procedural phases of plan 800 may represent exemplary procedural phases for whatever type of surgical procedure plan 800 may correspond with. For example, if plan 800 is for a partial nephrectomy such as the example described above, the procedural phases may represent phases that are planned to be performed during the partial nephrectomy. While five procedural phases are shown in the example of FIG. 8, it will be understood that more or fewer phases may be planned in other examples as may serve a particular implementation or surgical procedure.

Various potential augmentations are listed along the left column of the chart included in plan 800, and check marks are used to indicate if each potential augmentation is to be implemented during each procedural phase in the plan. Accordingly, when the operational context of the surgical procedure is identified to indicate which procedural phase is ongoing at a particular moment, system 100 may be configured to process the image presented to the user in accordance with whatever augmentations are indicated in plan 800. For example, as shown, in procedural phase 1, system 100 may provide the raw image to the user without any augmentation. In procedural phase 2, system 100 may augment the image to overlay a 3D model of subsurface anatomical structures ("Show 3D model (subsurface anatomy)"). In procedural phase 3, system 100 may continue with the subsurface anatomy model augmentation, while also adding an overlay of a 3D model of surface objects present at the surgical site such as instruments that may be occluded by smoke or another obscurant ("Show 3D model (instrument)"). In procedural phase 4, both of the 3D model augmentations may continue to be provided while certain anatomical features (e.g., features that may have become obscured by blood or fat during the surgical procedure) are emphasized with an additional augmentation ("Emphasize anatomy"). In procedural phase 5, system 100 may cease emphasizing the anatomy while continuing to overlay the 3D models. Additionally, system 100 may emphasize instrumentation and/or other objects such as needles and thread that may be used at this stage of the procedure ("Emphasize instrument", "Emphasize other object").

Using a surgical procedure plan such as plan 800, system 100 may be configured to provide surgical assistance based on operational context of a surgical procedure using various helpful augmentations such as have been described. As has been mentioned above, for example, system 100 may provide surgical assistance in any of the following ways or in a variety of other ways described herein.

For example, if system 100 detects that a suturing phase of a surgical procedure is ongoing and/or that a needle is present in the surgeon's view, the needle and corresponding thread may be highlighted or otherwise augmented or emphasized using augmentations overlaid onto the surgeon's view. This may help the surgeon keep focus on the needle and sutures that are being stitched, to easily retrieve the needle if dropped, and so forth.

As another example, if system 100 detects that a cauterizing phase of a surgical procedure is ongoing and/or that smoke is present in the surgeon's view, edges of instruments may be highlighted or otherwise augmented or emphasized using augmentations overlaid onto the surgeon's view. This may help the surgeon easily see the instruments even as smoke might otherwise obscure or partially obscure them from view.

As yet another example, if system 100 detects that anatomy is clearly visible (e.g., without a large amount of fat, smoke, or other obscurant present) in the scene, certain augmentations may be displayed that would otherwise be difficult to properly register to the target anatomy (due to the obscurants). Such augmentations may not, however, be presented when obscurants that are present prevent the system from achieving a suitable registration if it is determined that a potentially misaligned augmentation may be the source of more distraction than assistance to the user.

In addition to augmenting the image presented to the user, system 100 may further be configured to perform other operations or tasks based on the operational context of a surgical procedure once that context has been identified. For example, system 100 may be configured to request suction if blood or smoke are detected at the surgical site by, for example, generating a notification to be seen by the surgical team that such suction should be considered. As another example, system 100 may be configured to automatically request a sample bag if operational context is identified indicating that a piece of tissue has been resected that will need to be bagged. As yet another example, system 100 may request a suturing needle, clamps, or other such tools when bleeding is detected, and/or may request additional sutures and more thread as appropriate when it is detected that an end of the thread has been reached. In some such examples, system 100 may request a particular length of thread based on the operational context of how many more sutures are detected to be needed.

As another example of an action that system 100 may be configured to perform based on identified operational context, system 100 may enable or adjust the parameters of a particular imaging modality if, based on the operational context, system 100 determines that such would be helpful. For instance, system 100 may enable or adjust the parameters of a doppler ultrasound module used for imaging vasculature if operational context is identified indicating that arterial clamping is about to be performed. System 100 may also switch back to normal ultrasound mode (e.g., without doppler, etc.) when such clamping is complete.

System 100 may also adjust visualization parameters based on operational context that has been identified. For instance, system 100 may use computer vision to estimate tissue surface properties, and may use the identified properties to adjust rendering parameters such as sub-surface scattering. Subsurface scattering is just one an example of a physical property that may potentially be measured in-vivo and used to create more realistic visualizations, but it will be understood that various other examples may also be used in certain implementations. For instance, the visualization presented to a user may be altered to provide good contrast between the overlay and background, or to not show certain (or any) 3D models on top of unstable tissues like fatty tissues.

Figure 9:
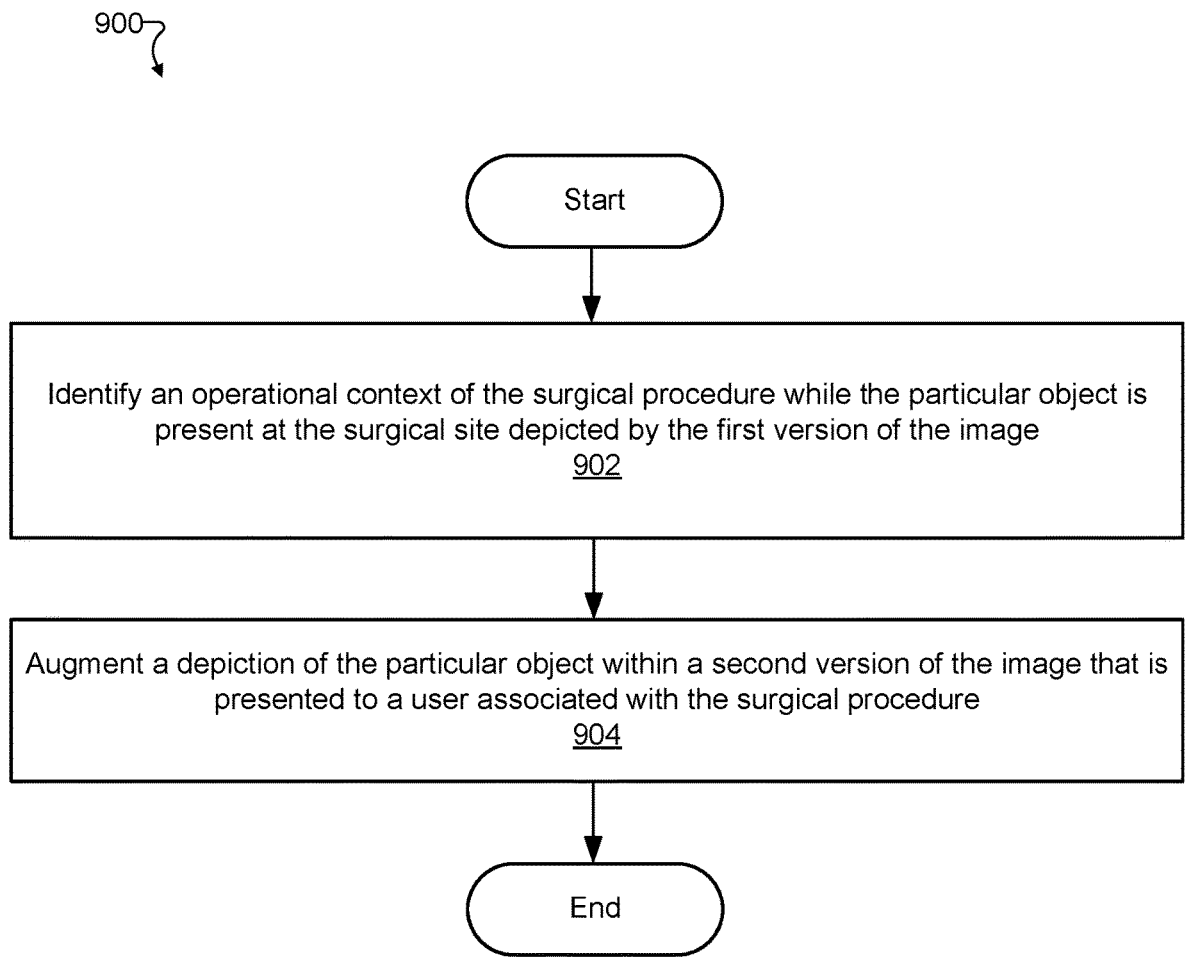
FIG. 9 illustrates an exemplary method for providing surgical assistance based on operational context of a surgical procedure according to principles described herein.

FIG. 9 illustrates an exemplary method 900 for providing surgical assistance based on operational context of a surgical procedure. While FIG. 9 illustrates exemplary operations according to one embodiment, other embodiments may omit, add to, reorder, combine, and/or modify any of the operations shown in FIG. 9. One or more of the operations shown in FIG. 9 may be performed by a contextual assistance system during a surgical procedure. For example, the contextual assistance system performing the operations shown in FIG. 9 may be implemented by system 100, any components included therein, and/or any implementation thereof.

In operation 902, a contextual assistance system may identify an operational context of a surgical procedure. For instance, the operational context may be identified while a particular object is present at a surgical site depicted by a first version of an image. In some examples, the contextual assistance system may perform operation 902 during the surgical procedure. Operation 902 may be performed in any of the ways described herein.

In operation 904, the contextual assistance system may augment a depiction of the particular object within a second version of the image. The second version of the image may be presented to a user associated with the surgical procedure, and the augmenting of the depiction of the particular object within the second version of the image may be based on the operational context identified in operation 902. In some examples, the contextual assistance system may perform operation 904 during the surgical procedure. Operation 904 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 10:
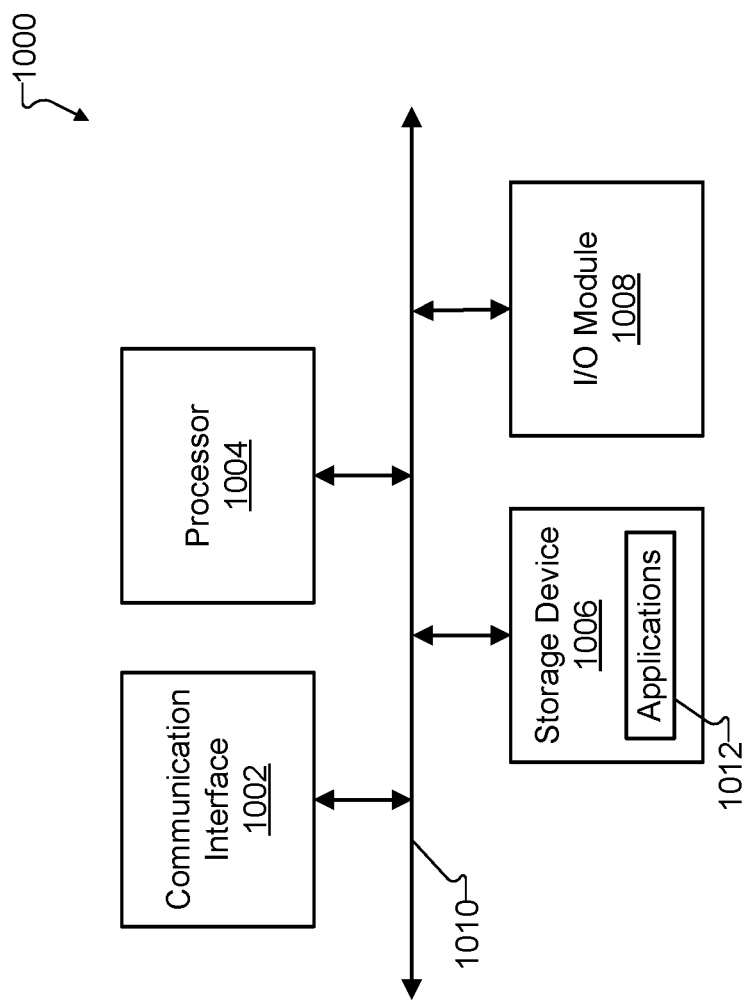
FIG. 10 illustrates an exemplary computing device according to principles described herein.

FIG. 10 illustrates an exemplary computing device 1000 that may be specifically configured to perform one or more of the processes described herein. Any of the systems, units, computing devices, and/or other components described herein may be implemented by computing device 1000.

As shown in FIG. 10, computing device 1000 may include a communication interface 1002, a processor 1004, a storage device 1006, and an input/output ("I/O") module 1008 communicatively connected one to another via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data and/or interpreting, executing, and/or directing execution of one or more of the instructions, processes, and/or operations described herein. Processor 1004 may perform operations by executing computer-executable instructions 1012 (e.g., an application, software, code, and/or other executable data instance) stored in storage device 1006.

Storage device 1006 may include one or more data storage media, devices, or configurations and may employ any type, form, and combination of data storage media and/or device. For example, storage device 1006 may include, but is not limited to, any combination of the non-volatile media and/or volatile media described herein. Electronic data, including data described herein, may be temporarily and/or permanently stored in storage device 1006. For example, data representative of computer-executable instructions 1012 configured to direct processor 1004 to perform any of the operations described herein may be stored within storage device 1006. In some examples, data may be arranged in one or more databases residing within storage device 1006.

I/O module 1008 may include one or more I/O modules configured to receive user input and provide user output. I/O module 1008 may include any hardware, firmware, software, or combination thereof supportive of input and output capabilities. For example, I/O module 1008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct an implementation of processor 1004 to perform one or more operations or functions associated with processing facility 104 of system 100. Likewise, storage facility 102 of system 100 may be implemented by or within an implementation of storage device 1006.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
identify, during a surgical procedure, an operational context of the surgical procedure while a particular object is present at a surgical site depicted by a first version of an image;
access content associated with the particular object; and
augment, based on the identified operational context, a depiction of the particular object within a second version of the image that is presented to a user associated with the surgical procedure, the augmenting of the depiction of the particular object including displaying at least a portion of the content associated with the particular object within the second version of the image.

2. The system of claim 1, wherein:
the user associated with the surgical procedure is a member of a surgical team performing the surgical procedure; and
the processor is further configured to execute the instructions to provide, during the surgical procedure, the second version of the image to a presentation system viewed by the member of the surgical team to thereby be presented to the user.

3. The system of claim 1, wherein the processor is further configured to execute the instructions to detect that the particular object is present at the surgical site by:
analyzing, using a computer-vision-based object recognition technology, the first version of the image; and
determining, based on the analyzing of the first version of the image using the computer-vision-based object recognition technology, that the particular object is present at the surgical site depicted by the first version of the image.

4. The system of claim 1, wherein the processor is further configured to execute the instructions to detect that the particular object is present at the surgical site by:
   accessing procedural data indicating that the particular object is held by a particular manipulator arm controlled by a computer-assisted surgical system;
   accessing kinematic data indicative of a pose of the manipulator arm with respect to an image capture device capturing the first version of the image; and
   determining, based on the procedural data and the kinematic data, that the particular object is present at the surgical site depicted by the first version of the image.

5. The system of claim 1, wherein:
   the identifying of the operational context includes determining, at a particular time during the surgical procedure, that the surgical procedure is in a particular procedural phase of a plurality of predefined procedural phases that are planned to be performed as part of the surgical procedure; and
   the processor is further configured to execute the instructions to detect, at or after the particular time and in response to the determining that the surgical procedure is in the particular procedural phase, that the particular object is present at the surgical site depicted by the first version of the image.

6. The system of claim 1, wherein the identifying of the operational context includes:
   accessing procedural data representative of at least one of a surgical instrument employed in performing the surgical procedure, a pose of the surgical instrument during the surgical procedure, audio content recorded in an operating room during the surgical procedure, image content recorded in the operating room during the surgical procedure, or user input provided by a member of a surgical team performing the surgical procedure; and
   determining, based on the procedural data, that the surgical procedure is in a particular procedural phase of a plurality of predefined procedural phases that are planned to be performed as part of the surgical procedure.

7. The system of claim 1, wherein the identifying of the operational context includes detecting that an obscurant present at the surgical site is at least partially obscuring a view of the particular object as depicted by the first version of the image, the obscurant including at least one of blood, fat, or smoke.

8. The system of claim 1, wherein the augmenting of the depiction of the particular object within the second version of the image comprises modifying, from the first version of the image and based on the content associated with the particular object, a depiction of the particular object so as to emphasize the depiction of the particular object in the second version of the image.

9. The system of claim 1, wherein:
   the content associated with the particular object includes a predefined model of the particular object; and
   the augmenting of the depiction of the particular object within the second version of the image comprises displaying, within the second version of the image in place of the depiction of the particular object captured within the first version of the image, a representation of the particular object that is based on the content.

10. The system of claim 1, wherein:
    the content associated with the particular object includes a predefined model of a subsurface object present at the surgical site but not depicted in the first version of the image, the predefined model generated using preoperative scan data captured prior to the surgical procedure; and
    the augmenting of the depiction of the particular object within the second version of the image comprises displaying, within the second version of the image in addition to the depiction of the particular object captured within the first version of the image, a representation of the subsurface object based on the content.

11. A method comprising:
    identifying, by a contextual assistance system during a surgical procedure, an operational context of the surgical procedure while a particular object is present at a surgical site depicted by a first version of an image;
    accessing content associated with the particular object; and
    augmenting, by the contextual assistance system based on the identified operational context, a depiction of the particular object within a second version of the image that is presented to a user associated with the surgical procedure, the augmenting of the depiction of the particular object including displaying at least a portion of the content associated with the particular object within the second version of the image.

12. The method of claim 11, wherein:
    the user associated with the surgical procedure is a member of a surgical team performing the surgical procedure; and
    the method further comprises providing, by the contextual assistance system during the surgical procedure, the second version of the image to a presentation system viewed by the member of the surgical team to thereby be presented to the user.

13. The method of claim 11, further comprising detecting, by the contextual assistance system, that the particular object is present at the surgical site by:
    analyzing, using a computer-vision-based object recognition technology, the first version of the image; and
    determining, based on the analyzing of the first version of the image using the computer-vision-based object recognition technology, that the particular object is present at the surgical site depicted by the first version of the image.

14. The method of claim 11, further comprising detecting, by the contextual assistance system, that the particular object is present at the surgical site by:
    accessing procedural data indicating that the particular object is held by a particular manipulator arm controlled by a computer-assisted surgical system;
    accessing kinematic data indicative of a pose of the manipulator arm with respect to an image capture device capturing the first version of the image; and
    determining, based on the procedural data and the kinematic data, that the particular object is present at the surgical site depicted by the first version of the image.

15. The method of claim 11, wherein the identifying of the operational context includes determining, at a particular time during the surgical procedure, that the surgical procedure is in a particular procedural phase of a plurality of predefined procedural phases that are planned to be performed as part of the surgical procedure; and
    further comprising detecting, by the contextual assistance system at or after the particular time and in response to the determining that the surgical procedure is in the particular procedural phase, that the particular object is present at the surgical site depicted by the first version of the image.

16. The method of claim 11, wherein the identifying of the operational context includes:
accessing procedural data representative of at least one of a surgical instrument employed in performing the surgical procedure, a pose of the surgical instrument during the surgical procedure, audio content recorded in an operating room during the surgical procedure, image content recorded in the operating room during the surgical procedure, or user input provided by a member of a surgical team performing the surgical procedure; and
determining, based on the procedural data, that the surgical procedure is in a particular procedural phase of a plurality of predefined procedural phases that are planned to be performed as part of the surgical procedure.

17. The method of claim 11, wherein the augmenting of the depiction of the particular object within the second version of the image comprises modifying, from the first version of the image and based on the content associated with the particular object, a depiction of the particular object so as to emphasize the depiction of the particular object in the second version of the image.

18. The method of claim 11, wherein:
the content associated with the particular object includes a predefined model of the particular object; and
the augmenting of the depiction of the particular object within the second version of the image comprises displaying, within the second version of the image in place of the depiction of the particular object captured within the first version of the image, a representation of the particular object that is based on the content.

19. The method of claim 11, wherein:
the content associated with the particular object includes a predefined model of a subsurface object present at the surgical site but not depicted in the first version of the image, the predefined model generated using preoperative scan data captured prior to the surgical procedure; and
the augmenting of the depiction of the particular object within the second version of the image comprises displaying, within the second version of the image in addition to the depiction of the particular object captured within the first version of the image, a representation of the subsurface object based on the content.

20. A non-transitory computer-readable medium storing instructions that, when executed, direct a processor of a computing device to:
identify, during a surgical procedure, an operational context of the surgical procedure while a particular object is present at a surgical site depicted by a first version of an image;
access content associated with the particular object; and
augment, based on the identified operational context, a depiction of the particular object within a second version of the image that is presented to a user associated with the surgical procedure, the augmenting of the depiction of the particular object including displaying at least a portion of the content associated with the particular object within the second version of the image.

* * * * *